United States Patent [19]

Pierpont

[11] Patent Number: 5,484,412
[45] Date of Patent: Jan. 16, 1996

[54] ANGIOPLASTY METHOD AND MEANS FOR PERFORMING ANGIOPLASTY

[76] Inventor: Brien E. Pierpont, 2028 Brightwaters Blvd., St. Petersburg, Fla. 33704

[21] Appl. No.: 229,545

[22] Filed: Apr. 19, 1994

[51] Int. Cl.⁶ .................................................. A61M 29/00
[52] U.S. Cl. ............................ 604/101; 604/102; 606/194
[58] Field of Search ............................ 604/96, 101, 102, 604/281, 246; 128/656–658; 606/194

[56] References Cited

U.S. PATENT DOCUMENTS

| | | | |
|---|---|---|---|
| 3,395,710 | 8/1968 | Stratton et al. | 604/270 |
| 4,581,017 | 4/1986 | Sahota | 604/101 |
| 4,744,366 | 5/1988 | Jang . | |
| 4,771,777 | 9/1988 | Horzewski et al. | 604/96 |
| 4,832,028 | 5/1989 | Patel . | |
| 4,932,959 | 6/1990 | Horzewski et al. | 604/96 |
| 5,019,042 | 5/1991 | Sahota | 604/101 |
| 5,035,705 | 7/1991 | Burns | 606/194 |
| 5,059,178 | 10/1991 | Ya | 604/96 |
| 5,085,636 | 2/1992 | Burns | 606/194 |
| 5,102,390 | 4/1992 | Crittenden et al. | 604/101 |
| 5,158,540 | 10/1992 | Wijay et al. | 604/101 |
| 5,178,608 | 1/1993 | Winters . | |
| 5,180,367 | 1/1993 | Kontos et al. | 604/101 |
| 5,299,575 | 4/1994 | Sandridge | 604/96 |

FOREIGN PATENT DOCUMENTS

| | | | |
|---|---|---|---|
| 0415332 | 3/1991 | European Pat. Off. | 128/657 |
| 0565996 | 10/1993 | European Pat. Off. . | |

Primary Examiner—C. Fred Rosenbaum
Assistant Examiner—Mark Bockelman
Attorney, Agent, or Firm—Zarley, McKee, Thomte, Voorhees & Sease

[57] ABSTRACT

An angioplasty procedure wherein a balloon dilatation catheter is movably positioned within an anchoring catheter which in turn is located within a guiding catheter. Internal balloons in the anchoring catheter can be inflated to anchor it to the balloon dilatation catheter. External balloons on the anchoring catheter can be inflated to anchor it to the inside of the guiding catheter. The balloons can be selectively inflated and deflated. Other external balloons on the inner end and outer surface can be inflated to secure the anchoring catheter within the blood vessel beyond the inner end of the guiding catheter. Perforations appear in the anchor catheter to permit blood to flow inside and outside thereof. An angioplasty method whereby a conventional guide catheter is inserted into the blood vessel to a location just short of the narrowed portion of the blood vessel. The conventional guide wire, balloon dilatation catheter, and anchoring catheter are then inserted through the guiding catheter with the anchoring catheter and balloon dilatation catheter being secured together by the internal balloons on the anchor catheter. As the point of treatment in the blood vessel is approached, the internal balloons are collapsed, and the spaced external balloons are inflated, thus securing the anchoring catheter to both the guiding catheter and the interior of the blood vessel. The balloon dilatation catheter is then extended from the anchoring catheter to perform to conventional function with respect to the narrowed section of the blood vessel.

20 Claims, 4 Drawing Sheets

ANGIOPLASTY METHOD AND MEANS FOR PERFORMING ANGIOPLASTY

BACKGROUND OF THE INVENTION

Cardiac catheterization and angioplasty are common medical procedures. The coronary arteries are vessels which supply the heart muscle with blood and are located on the outside surface of the heart. In order to visually examine the coronary arteries, a contrast agent has to be injected into the vessels before x-ray pictures can be taken of them. This is accomplished through a procedure called cardiac catheterization. This contrast agent is delivered through a catheter, which is a small hollow tube. This catheter is advanced to the heart under x-ray guidance, usually being inserted at the level of the groin into the femoral artery. This is accomplished through a needle which is first advanced into the femoral artery and subsequently the catheter is passed through the needle into the blood vessel or femoral artery. The femoral artery in turn is a tributary of the great vessel originating in the heart and therefore the catheter can be passed in a retrograde fashion under x-ray guidance very easily back to the origin of the coronary arteries.

Once the catheter is positioned at the origin of the coronary arteries, a dye syringe is placed on the end of the catheter remaining outside the patient and injections are performed with simultaneous x-ray pictures being taken.

An angioplasty procedure is similar in technique but more invasive, by the fact that a smaller catheter with a deflated balloon on its tip is advanced through the catheter which is positioned at the origin of the coronary artery and advanced down into the coronary artery to the site of where the vessel is narrowed. The balloon dilatation catheter is not advanced down the coronary artery by itself, however, first, a very small guide wire is advanced down the coronary artery, across the narrowed segment and then advanced further down into the coronary artery, beyond the narrowed segment. The balloon dilatation catheter is then advanced over the guide wire to the site of the narrowing. The guide wire allows the balloon dilatation catheter to track over it, thereby facilitating advancement of the balloon dilatation catheter down the vessel and thus preventing damage to the vessel wall. Once the balloon is positioned at the site of the narrowing in the vessel, the balloon is inflated by means of a hand held balloon inflation device. The balloon is inflated for generally two to three minutes and then deflated and withdrawn. This compresses the fatty-like material which is responsible for narrowing the coronary artery and opens the vessel, allowing for proper blood flow to the heart muscle.

At times it is difficult to advance the balloon dilatation catheter to the site of the narrowing, as these vessels are not always straight and often times bends in the vessel have to be negotiated before reaching the point of narrowing. Frequently, the balloon dilatation catheter cannot be easily advanced and the guiding catheter which is housing the balloon dilatation catheter and the guide wire, comes loose from its position at the origin of the coronary artery and does not provide enough structural support or backup to allow advancement of the balloon dilatation catheter to the narrowed site.

The purpose of my invention is to secure the guiding catheter to its position in the origin of the coronary artery, (coronary ostium), so that the balloon dilatation catheter can be housed therein and advanced forwardly into the coronary artery without losing structural support or backup from the guiding catheter. When the guiding catheter remains in a fixed position, it facilitates immensely the ability to advance the balloon dilatation catheter. At times angioplasties are unsuccessful purely on the basis of not being able to find a guiding catheter which will allow enough structural support to advance the balloon dilatation catheter properly.

It is therefore a principal object of this invention to provide a method and means to secure or anchor the guiding catheter in the origin of the coronary artery so that the balloon dilatation catheter can be easily advanced therefrom into the coronary artery without losing its structural support from the guiding catheter.

SUMMARY OF THE INVENTION

This invention comprises an angioplasty procedure wherein the balloon dilatation catheter is movably positioned within an anchoring catheter which in turn is located within a guiding catheter. Internal balloons in the anchoring catheter can be inflated to secure it to the balloon dilatation catheter. External balloons on the anchoring catheter can be inflated to anchor it to the inside of the guiding catheter. The external fixation balloons can be selectively inflated and deflated from the internal fixation balloons. Other external balloons on the distal end and outer surface can be inflated to secure the anchoring catheter within the blood vessel beyond the distal end of the guiding catheter. Perforations appear in the anchoring catheter to permit blood to flow inside and outside thereof.

The method of this invention inserts a conventional guiding catheter into the origin of the coronary artery, (coronary ostium). The conventional guide wire, conventional balloon dilatation catheter, and anchoring catheter are then inserted through the guiding catheter with the anchoring catheter and balloon dilatation catheter being secured together by the internal fixation balloons on the anchoring catheter. As the balloon dilatation catheter and anchoring catheter are advanced over the guide wire and into the coronary artery, the internal fixation balloons are deflated and the spaced external fixation balloons are inflated, thus securing the anchoring catheter to both the guiding catheter and the interior of the proximal portion of the coronary artery. This therefore serves to secure the guiding catheter to the origin of the coronary artery. The balloon dilatation catheter is then extended from the anchoring catheter tracking over the guide wire to perform the conventional function with respect to the narrowed section of the blood vessel.

DESCRIPTION OF THE PREFERRED EMBODIMENT

Figure 1:
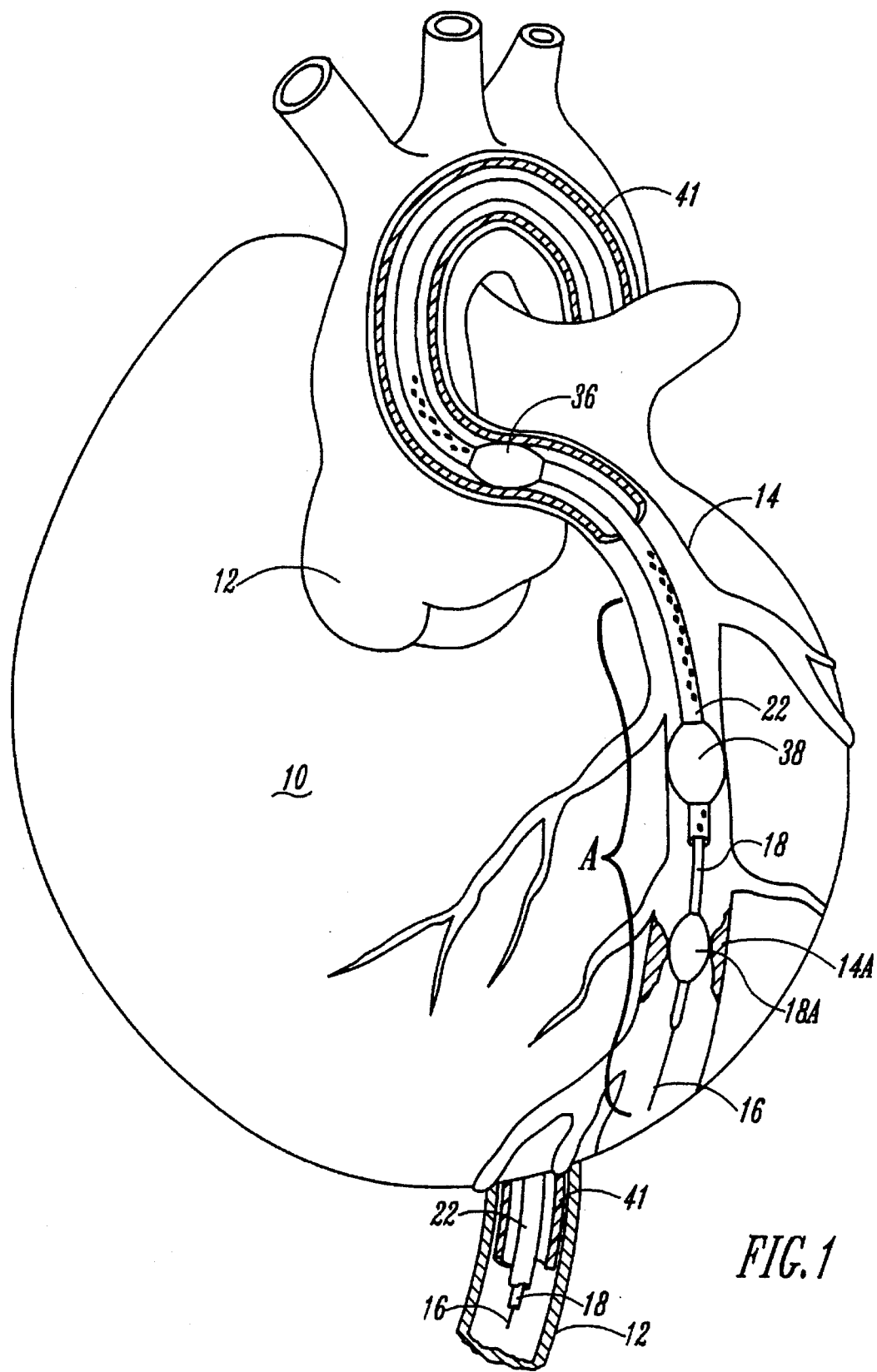
FIG. 1 is a schematic view of a human heart with the apparatus of this invention inserted into a coronary artery.

FIG. 1 shows a schematic view of a heart muscle 10 connected to the primary blood supply vessel 12 (aorta). A coronary artery 14 is also depicted in FIG. 1. The numeral 14A in FIG. 1 and FIG. 5 shows the plaque or obstruction in the coronary artery 14.

Figure 4:
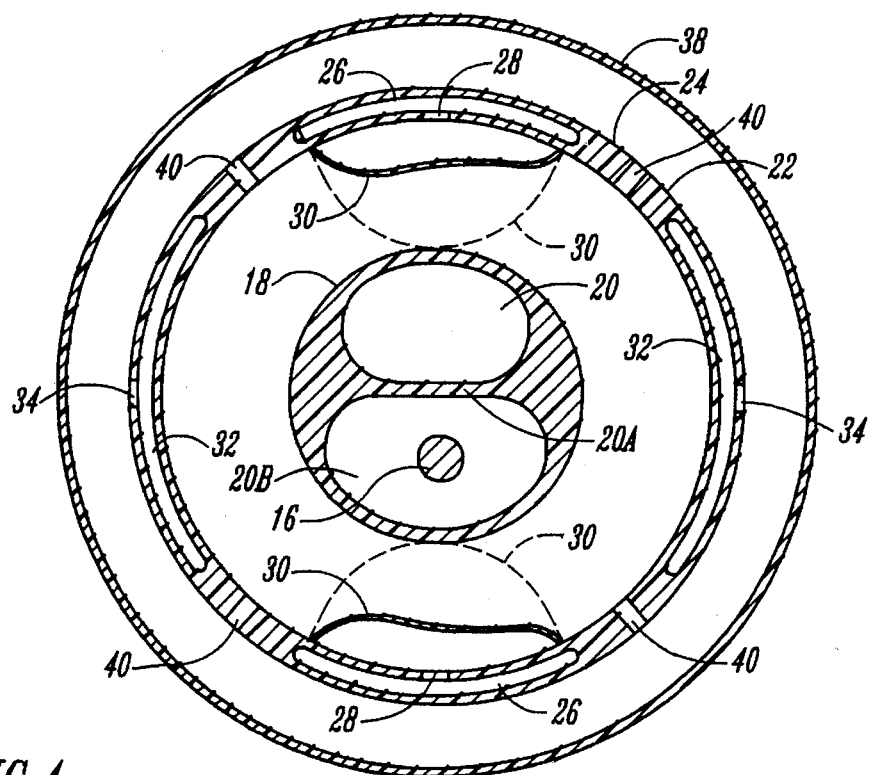
FIG. 4 is a typical cross-sectional view at an enlarged scale taken on line 4—4 of FIG. 3.
Figure 5:
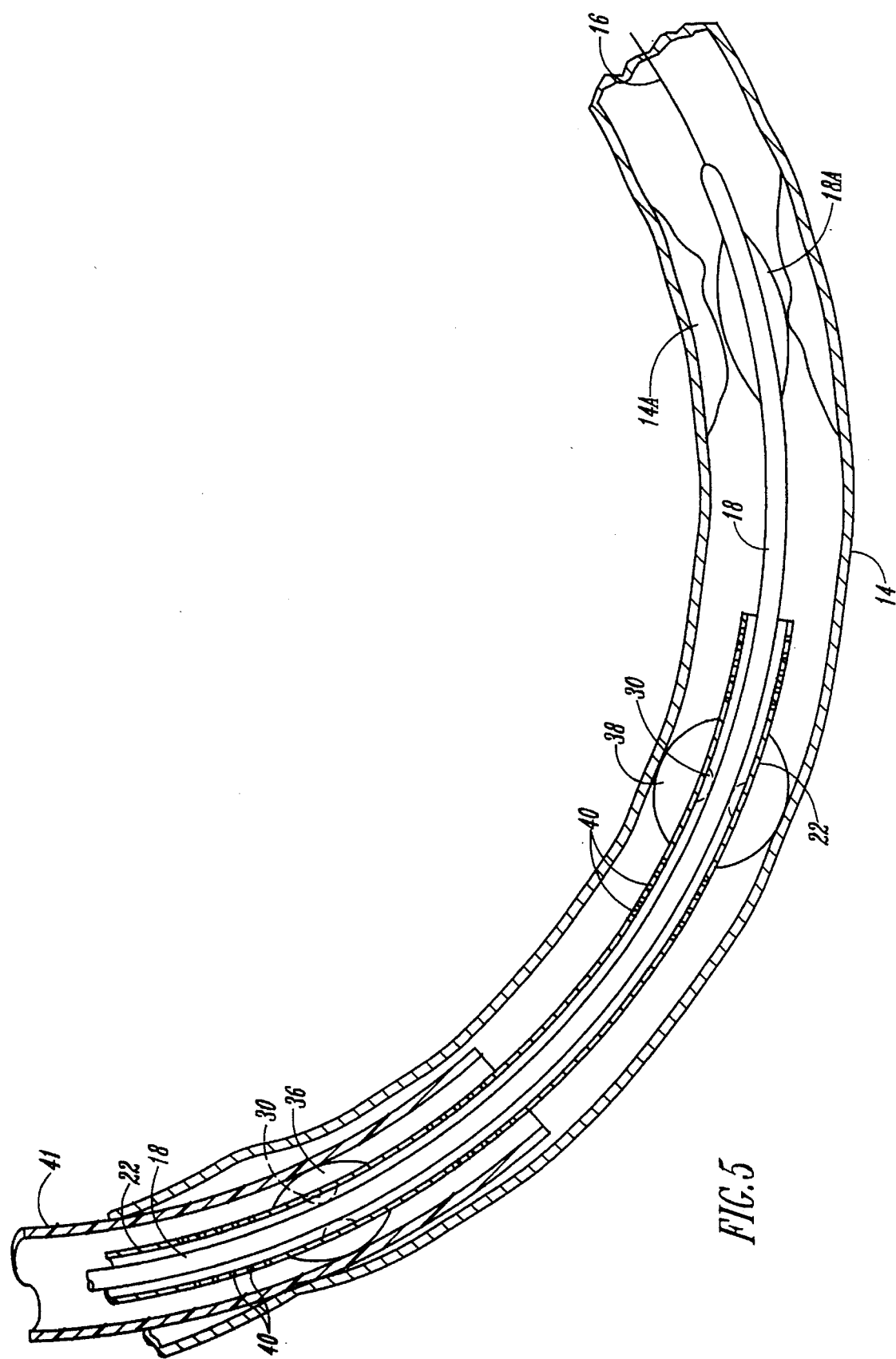
FIG. 5 is an enlarged scale sectional view of FIG. 2.

With reference to FIG. 5, the numeral 16 reveals a conventional guide wire 16 over which a balloon dilatation catheter 18 is slidably mounted. Catheter 18 has an inflatable balloon 18A on the distal end thereof. Catheter 18 has its internal diameter divided by membrane 20A to create a balloon inflation passageway 20 and a guide wire passageway 20B (FIG. 4).

Balloon dilatation catheter 18 is slidably mounted within the hollow interior of anchoring catheter 22. The outer wall 24 of anchoring catheter 22 has two hollow elongated internal balloon inflation passageways 26, each of which has a better artistic definition port 28. Two pairs of flexible internal balloons 30 extend inwardly within the hollow interior of the anchoring catheter 22 and extend over ports 28.

Similarly, the outer wall 24 of anchor catheter 22 has two external balloon passageways 32 (FIG. 4) each of which have external ports 34 in (FIG. 4). A first concentric external balloon 36 extends outwardly from wall 24 over a first pair of ports 34, and a second concentric balloon 38 extends over a second pair of ports 34. As also seen in FIG. 4, a plurality of blood perfusion ports 40 extend through wall 24 of anchoring catheter 22 on opposite sides of balloons 36 and 38.

The numeral 41 (FIG. 5) designates a guiding catheter whose function will be described hereafter.

Figure 6:
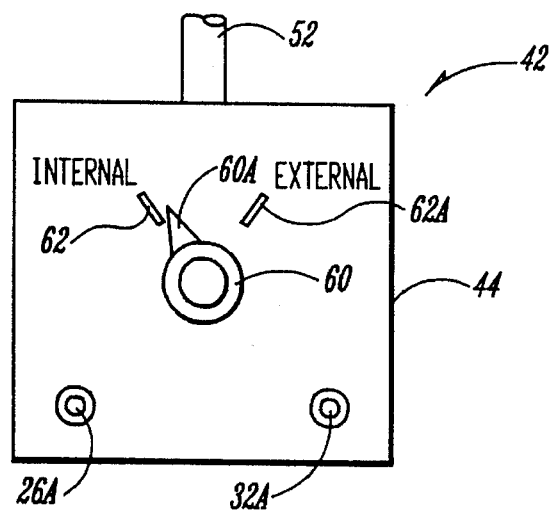
FIG. 6 is an end elevational view of an inflation valve for the internal and external balloons of the anchoring catheter.
Figure 7:
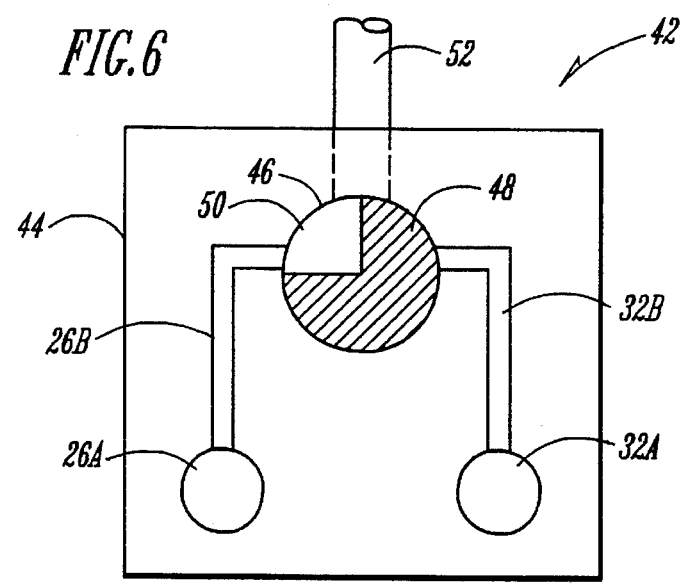
FIG. 7 is a schematic sectional view through the valve of FIG. 6 when the internal balloons are inflated.

FIG. 6 shows an end elevation of a balloon inflation valve 42 which has a body 44 depicted in FIG. 7. A horizontal bore 46 extends into body 44 and rotatably supports spool 48 which has an elongated 90 degree notch 50 which is in communication with a contrast agent inlet 52 which is also in communication with bore Horizontal bores 26A and 32A also extend into body 44 and are adapted to be connected (not shown)) with internal balloon inflation passageways 26 and external balloon inflation passageways 32, respectively.

Figure 3:
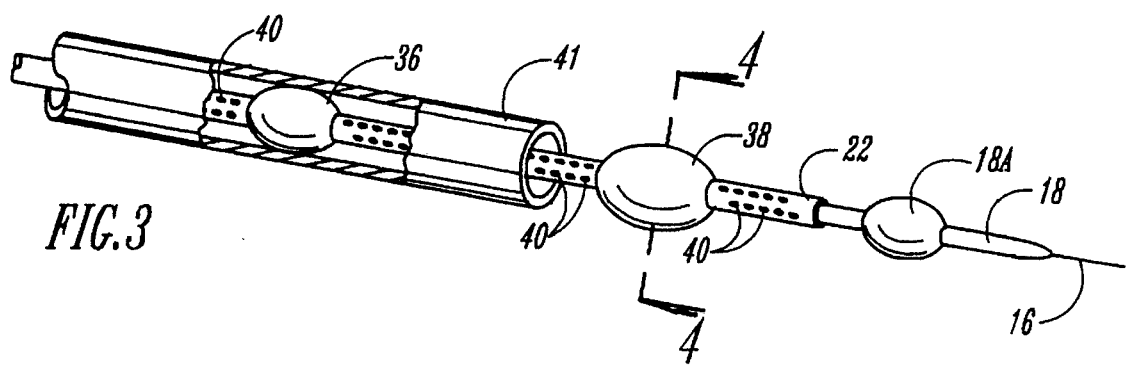
FIG. 3 is a large scale sectional-perspective view of the forward or distal ends of the balloon dilatation, anchoring and guiding catheters.
Figure 8:
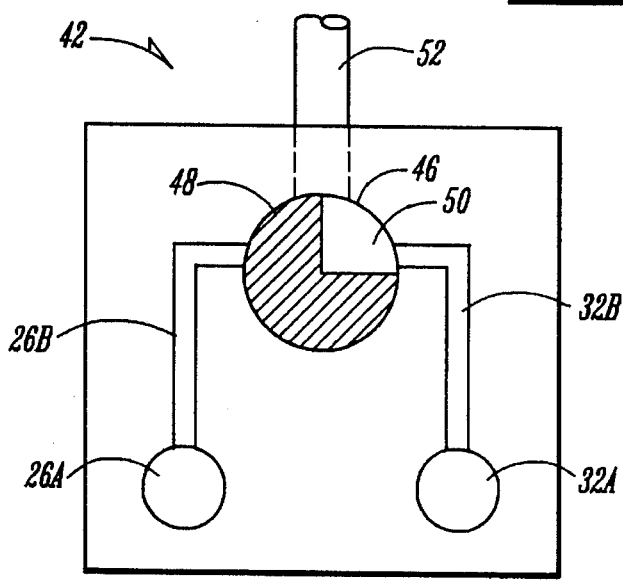
FIG. 8 is a schematic sectional view through the valve of FIG. 6 when the external balloon of the anchoring catheter are inflated.

A conventional knob 60 (FIG. 6) is mounted on the outer end of spool 48 (FIG. 7) and has a guide tab 60A thereon which is adapted to engage stop element 62 or 62A which are embossed on the outer face of body 44 as shown in FIG. 6. When tab 60A engages stop element 62, the spool 48 is in the position of FIG. 7 to introduce contrast agent through passageway 52, bore 46, and passageway 26B to introduce air under pressure into bore 26A whereupon the internal balloon inflation passageways 26 will receive a source of contract agent to inflate the flexible internal balloons 30 of anchoring catheter 22. When the spool 48 is changed from the position of FIG. 7, as just described, to the position of FIG. 8, contrast agent is introduced in a similar manner but through passageway 32A to cause the two external balloons 36 (depicted in FIG. 3) and 38 to inflate in like manner. It should be noted that when the valve spool 46 is moved from the position of FIG. 7 to FIG. 8, or vice versa, only one of the passageways 26A or 32A will have contrast agent, while contrast agent will be denied to the other of such passageways. The spool will allow only the internal balloons or the external balloons to inflate, but not both at the same time. Thus, the valve 42 will guarantee that the internal and external balloons of the anchoring catheter 22 will not both be inflated simultaneously. This prevents any injury to the patient by preventing any shearing force which could be created if both sets of balloons were inflated simultaneously and an attempt to advance the balloon dilatation catheter was made resulting in dragging the anchoring catheter and externally inflated balloons along with it.

In operation, the guiding catheter 41 is inserted into the groin of the patient in the manner described above and positioned at the origin of the coronary artery 14. The balloon dilatation catheter 18 is inserted over guide wire 16, and both the guide wire 16 and balloon dilatation catheter 18 are then inserted within anchoring catheter 22. The assembled guide wire 16, balloon dilatation catheter 18 and anchoring catheter 22 are moved as a unit into guiding catheter 41 after the internal fixation balloons 30 of the anchoring catheter have been inflated in the manner described. At this point in time, the external balloons 36 and 38 of anchoring catheter 22 are still deflated. The above described assembled components are extended through the guiding catheter until the guide wire 16 and the distal end of the anchoring catheter 22 extend distally beyond the distal end of the guiding catheter. At that point in time, the internal balloons 30 are deflated in the manner described by valve 42 and the external balloons 36 and 38 are inflated. The external balloon 38 engages the inner wall of coronary artery 14, while the external balloon 36 engages the interior of the guiding catheter 41. This secures the guiding catheter 41 to the coronary artery 14.

Figure 2:
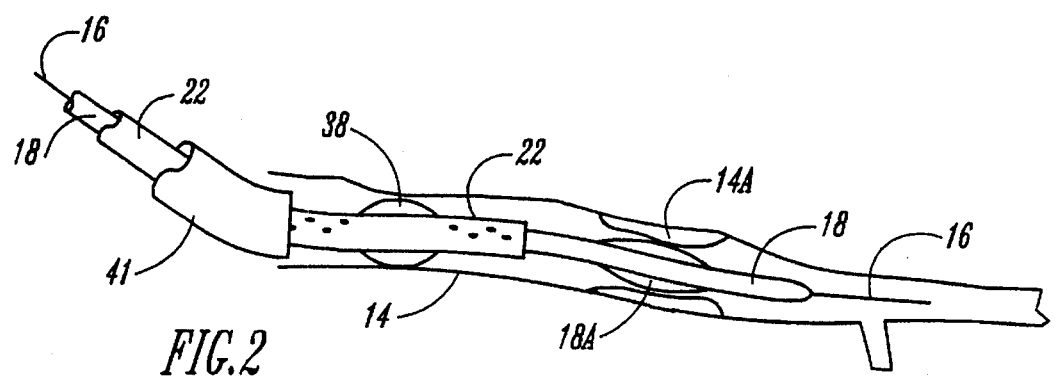
FIG. 2 is an enlarged scale schematic view of the segment A in FIG. 1.

With deflation of the internal fixation balloons, the balloon dilatation catheter 18 is now movable independent of the anchoring catheter and is thereupon moved to the position shown in FIGS. 1, 2 and 5 so that the balloon 18A is adjacent the plaque 14A. This can be easily accomplished by the reason of the fact that the anchoring catheter is secured both to the internal wall of the blood vessel and to the internal surface of the guiding catheter 41, anchoring the guiding catheter to the coronary ostium, thus providing backup support for advancement of the balloon dilatation catheter over the guide wife. The balloon 18A is then inflated in the conventional manner to treat the plaque 14A. After this has been done, the external balloons 36 and 38 are deflated, and the respective catheters can be removed in the conventional fashion.

The perfusion ports 40 allow for blood to flow through the anchoring catheter and down the coronary artery while the balloons are inflated. This is very critical so as to continue to support the heart muscle 10 with oxygen while the balloons are inflated and anchoring the guiding catheter to the coronary artery.

It is therefore seen that this invention will accomplish at least all of its stated objectives.

I claim:

1. A catheter assembly, comprising, an elongated hollow anchoring catheter having a distal end, and a tubular wall with inner and outer surfaces, a hollow guiding catheter having a distal end and a proximal end housing said anchoring catheter, a first anchoring balloon member attached to the outer surface of said tubular wall of the anchoring catheter and adapted upon inflation to project outwardly from said tubular wall to engage the guiding catheter and secure said anchoring catheter within said guiding catheter, an elongated balloon dilatation catheter longitudinally extending through said anchoring catheter and having a distal end, a dilatation balloon attached to the distal end of said balloon dilatation catheter, a second anchoring balloon member attached to the inner surface of said tubular wall and adapted upon inflation to project inwardly from said tubular wall of the anchoring catheter to engage and retain said dilatation catheter against movement with respect to said anchoring catheter, means associated with said catheter assembly for independently inflating and deflating said first and second anchoring balloon members;

means for inflating the dilatation balloon; and a guide wire extending through the dilatation catheter and along which the dilatation catheter is slidable.

2. The assembly of claim 1 further comprising a third anchoring balloon member attached to the outer surface of the tubular wall of the anchoring catheter and adapted upon inflation to project outwardly to engage the blood vessel and secure the anchoring catheter to the blood vessel, and whereby upon inflation of the first and third balloon members the guiding catheter is operatively secured to the blood vessel.

3. The assembly of claim 1 wherein a longitudinally spaced pair of said second anchoring balloon members are attached to said tubular wall of the anchoring catheter.

4. The assembly of claim 1 wherein a pair of each of said first and second balloon members are attached to said tubular wall of the anchoring catheter.

5. The assembly of claim 1 wherein blood by-pass means are located in said tubular wall on opposite sides of at least one of said first or second anchoring balloon members.

6. The assembly of claim 1 wherein a longitudinally spaced pair of said first anchoring balloon members are attached to said tubular wall of the anchoring catheter.

7. The catheter assembly of claim 6 wherein one of the pairs of first anchoring balloon members secures said anchoring catheter to the blood vessel.

8. The method of use of the assembly of claim 1 wherein said guiding catheter is inserted into a blood vessel, said second balloon member is inflated to anchor said balloon dilatation catheter within said anchoring catheter, moving said anchoring catheter through said guiding catheter, deflating said second anchoring balloon member, and inflating said first anchoring balloon member to anchor said anchoring catheter within said guiding catheter; moving the dilatation catheter out of the distal end of the anchoring catheter and along the guide wire to said narrowed portion of the blood vessel, and treating said narrowed portion.

9. The method of use of claim 8 wherein a third balloon member is attached to said tubular wall of the anchoring catheter beyond the end of said guide catheter and is inflated with the first balloon member to secure said anchoring catheter to said blood vessel.

10. A catheter assembly, comprising:

a hollow guiding catheter;

a hollow anchoring catheter extensible through the guiding catheter;

a dilatation catheter extensible through the anchoring catheter;

a guide wire extending through the dilation catheter and along which the dilatation catheter is slidable;

a first external balloon attached to the anchoring catheter adapted to expand radially outwardly upon inflation to engage the guiding catheter and fix the anchoring catheter against movement relative to the guiding catheter;

a second external balloon attached to the anchoring catheter longitudinal spaced from the first external balloon and adapted to expand radially outwardly upon inflation to engage the blood vessel wall and fix the anchoring catheter against movement relative to the blood vessel;

a dilatation balloon attached to the dilatation catheter adapted to expand radially outwardly upon inflation to dilate a narrowed segment of the blood vessel wall;

first inflation means for inflating the first and second exterior balloons so as to anchor the anchoring catheter to the guiding catheter and to the blood vessel wall and thereby anchor the guiding catheter against movement relative to the blood vessel wall;

second inflation means for inflating the dilatation balloon.

11. The catheter assembly of claim 10 further comprising an internal balloon attached to the anchoring catheter adapted to expand radially inwardly upon inflation to engage the dilatation catheter and fix the anchoring catheter against movement relative to the dilatation catheter.

12. The catheter assembly of claim 11 wherein the first inflation means inflates the internal balloon independently of inflation of the external balloons.

13. The catheter assembly of claim 10 further comprising first and second perfusion ports in the anchoring catheter on opposite sides of the first external balloon to allow blood flow through the anchoring catheter while the first external balloon is inflated.

14. The catheter assembly of claim 10 further comprising first and second perfusion ports in the anchoring catheter on opposite sides of the second external balloon to allow blood flow through the anchoring catheter while the second external balloon is inflated.

15. A method for performing angioplasty, comprising:

inserting a guide wire through a dilatation catheter to form a dilatation catheter assembly;

inserting the dilatation catheter assembly into an anchoring catheter to form a unit;

inserting a guiding catheter into a patient such that the distal end of the guiding catheter is inserted into the origin of the patient's corollary artery;

inserting the unit through the guiding catheter;

extending the anchoring catheter partially out of the guiding catheter and into the blood vessel;

inflating a first external balloon attached to the anchoring catheter to secure the anchoring catheter to the guiding catheter;

inflating a second external balloon attached to the anchoring catheter to secure the anchoring catheter to the blood vessel such that the guiding catheter is effectively secured to the blood vessel;

sliding the guide wire further into the blood vessel;

sliding the dilatation catheter through the anchoring catheter and along the guide wire until a dilatation balloon attached to the dilatation catheter is adjacent a plaque area of the blood vessel;

inflating the dilatation balloon to treat the plaque area of the blood vessel.

16. The method of claim 15 further comprising allowing blood flow through perfusion ports in the anchoring catheter on opposite sides of the first external balloon.

17. The method of claim 15 further comprising allowing blood flow through perfusion ports in the anchoring catheter on opposite sides of the second external balloon.

18. The method of claim 15 further comprising deflating the first and second external balloons and withdrawing the dilatation catheter, guide wire, anchoring catheter and guiding catheter from the patient.

19. The method of claim 15 further comprising inflating an internal balloon in the anchoring catheter to secure the dilatation catheter therein prior to inserting the unit into the guiding catheter, and deflating the internal balloon prior to sliding the catheter assembly to the plaque area of the blood vessel.

20. The method of claim 15 wherein the first and second external balloons are inflated simultaneously.

* * * * *